(12) United States Patent
Braunstein et al.

(10) Patent No.: US 6,448,022 B1
(45) Date of Patent: Sep. 10, 2002

(54) PROTEIN WITH HUMAN CHORIOGONADOTROPIN INHIBITORY EFFECT

(75) Inventors: Glenn D. Braunstein, Santa Monica; Song-Guang Ren, Los Angeles, both of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 08/277,241

(22) Filed: Jul. 19, 1994

Related U.S. Application Data (63) Continuation of application No. 08/161,503, filed on Dec. 3, 1993, now abandoned, which is a continuation of application No. 07/806,914, filed on Dec. 13, 1991, which is a continuation of application No. 07/639,249, filed on Dec. 28, 1990, now Pat. No. 5,140,100.

(51) Int. Cl.$^7$ .......................... G01N 33/53; C07K 14/59
(52) U.S. Cl. .......................... 435/7.21; 436/65; 436/814; 436/818
(58) Field of Search ........................... 435/7.21; 436/65, 436/814, 818

(56) References Cited

U.S. PATENT DOCUMENTS

| | | | | |
|---|---|---|---|---|
| 4,558,035 A | * | 12/1985 | Johnson ........................ | 530/851 |
| 4,912,201 A | * | 3/1990 | Dizerega ...................... | 530/350 |
| 5,140,100 A | * | 8/1992 | Braunstein et al. ........... | 530/300 |

OTHER PUBLICATIONS

Kato et al, "Discordant Secretion of Placental Protein Hormones . . . " *J. Clin. Endo. Met.* 8(4): 814–820 (Apr. 1989).*

Yagel et al. "Interleukin–1 Stimulates Human Chorionic Gonadotropin . . . " *J. Clin. Endo. Met.* 68(5): 992–995 (May 1989).*

*Clinical Research*, vol. 38, No. 1, Jan. 1990, p. 148A, Thorofare, New Jersey, USA, Ren et al. "A Decidual Protein Inhibits Choriogonadotropin Release From Human Trophoblasts".

*Clinical Research*, vol. 38, No. 2, Apr. 1990, p. 298A, Thorofare, New Jersey, USA, Ren et al. "The Decidua Produces A Protein That Inhibits Choriogonadotropin Release From Human Trophoblasts".

*Placenta*, vol. 9, No. 2, 1998, pp. 109–115, Eastbourne, England, Vicovac et al., "Coincubation–An Experimental Approach To The Study of Decidual–Trophoblast Interaction".

*The Journal of Clinical Investigation*, vol. 876, No. 1, pp. 326–330, Jan. 1991, New York, USA Ren et al., "Decidua Produces A Protein That Inhibits Choriogonadotrophin Release From Human Trophoblasts".

* cited by examiner

*Primary Examiner*—Christine J. Saoud
(74) *Attorney, Agent, or Firm*—Lyon & Lyon LLP (57) ABSTRACT

A substance having an inhibitory effect on the production of human choriogonadotropin (hCG) is described, which comprises a protein isolated from human decidual cells with a preliminary amino acid analysis and a molecular weight of about 7,000 to about 10,000 daltons, and useful for use in inhibiting production of hCG in vivo or in vitro, may be measured as an indication of a cause of hCG inhibition, or used in the treatment of hCG-secreting tumors.

8 Claims, 5 Drawing Sheets

PROTEIN WITH HUMAN CHORIOGONADOTROPIN INHIBITORY EFFECT

This is a continuation of application(s) Ser. No. 08/161,503 filed on Dec. 3,1993 now abondoned "which is in turn a continuation of Ser. No. 07/806,914 filed Dec. 13, 1991, in turn a continuation-in-part of Ser. No. 07/639,249 filed on Dec. 28,1990. Now U.S. Pat. No. 5,140,100.

This invention relates to a decidual inhibitory protein (DIP) having an inhibitory effect on the production of human choriogonadotropin (hCG). More particularly, this invention relates to a protein isolated from human decidual cells with a preliminary amino acid analysis and a molecular weight of about 7,000 to about 10,000 daltons (as measured by ultrafiltration and gel chromatography) which may be used to inhibit hCG production in vivo (to induce abortion) or in vitro, measured in vivo or in vitro to diagnose the cause of hCG inhibition as an indication of potential miscarriage, or used in the treatment of hCG-secreting tumors.

BACKGROUND

The fetoplacental unit plays an essential role in the complicated hormonal interplay that is necessary for a successful pregnancy. Human choriogonadotropin (hCG), a hormone secreted by the trophoblast cells of the placenta, is present in the blood and urine during pregnancy. The primitive trophoblast begins producing hCG soon after fertilization and concentrations of hCG rise to peak values at 8–12 weeks of pregnancy, then decrease to a plateau level that is maintained during the remainder of the pregnancy. hCG may also be produced by certain trophoblastic or ectopic neoplasms.

Following fertilization, hCG stimulates the sustained secretion of progesterone by the corpus luteum, which is necessary for the growth of the uterine endometrium. hCG also is a stimulus for the production of fetal testicular androgens.

Decreased production of hCG can result in spontaneous abortion. Many abnormal pregnancies are associated with decreased levels of hCG as compared to normal pregnancies of the same duration. Most of these pregnancies end in spontaneous abortions. (B. Saxena, in *Endocrinology of Pregnancy*, Fuchs et al. Eds, Harper & Row, Philadelphia (1983) pp. 50–72).

The decidualized endometrium of the uterus also produces substances necessary for gestation. The decidualized endometrium and the placental trophoblast are contiguous tissues, and prior studies have investigated the possibility that each may influence the function of the other. Studies performed over a decade ago showed that hCG secretion from placental explants rose over the initial 72 hour period, leading researchers to suggest that loss of an endogenous hCG inhibitory factor (lost as it was removed from culture during changes of growth media) was responsible. (A. Golander et al., *Endocrinology* 102:597–605 (1978)). Yuen and coworkers have suggested that prolactin released by the decidua inhibits hCG production by trophoblasts. (B. H. Yuen, et al. *Am. J. Obstet. Gynecol.* 154:336–340 (1986)). Conversely, trophoblast hCG secretion has been found to be stimulated by interleukin-1 produced by placental phagocytic cells and decidual cells. (A. Flynn, et al., *Science*, 218:475–476 (1982) and S. Yagel et al., *J. Clin. Endocrinol. Metab.*, 68:992–995 (1989)).

Recently, Vicovac and Genvacev provided evidence, through co-incubation of trophoblasts and decidual cells, that the decidua has an inhibitory effect on the synthesis of hCG and total protein by trophoblast cells. (L. J. Vicovac et al., *Placenta* 9:109–115, (1988)). They concluded that some endometrial secretory product or products act to inhibit total protein synthesis and hCG secretion and/or synthesis by the trophoblast tissue.

Characterization of an endometrial hCG inhibitor was heretofore unknown. Potential uses for such a substance include as an agent to induce therapeutic abortions, as a basis to develop methods of evaluating hCG inhibition in vivo, or as a treatment of hCG-secreting tumors. The present inventors noted the inhibitory effect of a substance produced by decidual cells, and searched for the active material. As a result, the present inventors have found that a protein of a preliminary amino acid analysis and a molecular weight of about 7,000 to about 10,000 daltons (as measured by ultrafiltration and gel chromatography) is produced by the decidua and has an inhibitory effect on hCG production by the trophoblast and by JEG-3 choriocarcinoma cells.

SUMMARY OF THE INVENTION

The present invention is directed to a composition of matter which inhibits hCG production by human trophoblast cells and JEG-3 choriocarcinoma cells. The present invention is also directed to a method for inhibiting hCG release comprising contacting hCG producing tissue with an effective amount of the composition of the invention. The present invention is also directed to methods of evaluating hCG inhibition in vivo and in vitro, comprising quantifying the amount of the composition of the invention produced in vivo or in vitro.

The protein of the present invention may also be of use in the treatment of hCG-secreting tumors. Since the placental trophoblast is the normal site of synthesis of hCG, it is understandable that both gestational and nongestational trophoblastic tumors synthesize and secrete hCG. Indeed, hCG measurements have been quite useful for the diagnosis of these tumors, staging the tumors, and for monitoring the effects of therapy. In addition, some nontrophoblastic tumors may produce hCG ectopically. hCG may act as a growth factor for some tumors (Melmed S. and Braunstein GD: Human chorionic gonadotropin stimulates proliferation of Nb 2 rat lymphoma cells. *J. Clin. Endocrinol. Metab* 56:1068–1070, (1983)). Therefore, the use of a material which suppresses the production of hCG may suppress the growth of an hCG-secreting tumor. This has been previously shown with the use of anti-hCG antibodies in animal tumor models.

The present composition comprises a substantially-pure polypeptide of a preliminary amino acid analysis and a molecular weight of about 7,000 to about 10,000 daltons (as measured by ultrafiltration and gel chromatography), wherein said polypeptide inhibits the production of hCG by human trophoblast and JEG-3 choriocarcinoma cells. This polypeptide can be isolated from cultures of human decidual cells by cultivation and centrifugation of the culture medium. As used herein, "substantially pure" is intended to mean that DIP has been isolated from the decidual cells.

DETAILED DESCRIPTION OF THE INVENTION

The isolation and characterization of DIP will be further described by reference to the following detailed examples.

A. Materials and Methods
1. Preparation of Cells

Term placenta and associated membranes were obtained from 10 healthy pregnant women undergoing Cesarean section. Cytotrophoblasts were isolated from villus tissue using the method of H. J. Kliman et al., (*Endocrinology* 118:1567–1582 (1986)). Briefly, washed villus tissue was minced and then digested with 0.125% trypsin (Sigma, St. Louis, Mo.) and 0.2 g/L DNase (Sigma) at 37° C. for 30 min. Dispersed tissue was applied to a 5–70% percoll (Sigma) gradient. After centrifugation at 1200×g, the middle layer containing cytotrophoblasts was collected and washed. Decidual cells were isolated from decidual tissue dissected from placental membranes by the method of M. B. Braverman et al., (*J. Clin. Endocrinol. Metab.* 58:521–525 (1984)). This procedure involved the digestion of decidual tissue with 0.25% collagenase A (Mannhem, Indianapolis, Ind.) at 37° C. for 2 hours, followed by centrifugation through a 20–60% percoll gradient. Cell viability was greater than 90% using trypan blue exclusion. Human choriocarcinoma cell line JEG-3 was purchased from American Type Culture Collection (Rockville, Md.).

2. Cell Incubation

In co-culture studies, the trophoblast ($1 \times 10^6$ cells/ml/well) or decidual cells ($0.83-7.5 \times 10^5$ cells/ml/well), or trophoblast plus decidual cells (sum of both cell numbers/2ml/well) were cultured in 24-multiwell culture plates with 16 mm well diameter (Costar, Cambridge, Mass.) containing CMRL-1066 medium (GIBCO, Grand Island, N.Y.) supplemented with 10% fetal bovine serum (GIBCO), 25 mM HEPES (Sigma), 1 U/ml insulin (Nordisk, Gentofte, Denmark), 10 mM glutamine (Irving, Santa Ana, Calif.), 100 U/ml penicillin and 100 ug/ml streptomycin (GIBCO) in an atmosphere of 5% $CO_2$-95% air at 37° C. for 120 h. The medium was removed and replaced each 24 h.

In other studies, the trophoblast ($1 \times 10^6$ cells/2ml/well) or JEG-3 ($1 \times 10^5$ cells/2ml/well) were precultured for 24 hours. After removing the precultured medium, the cells were cultured in control medium or medium containing test substances. In all experiments, the media contained the same volume of CMRL-1066. In addition, in some trophoblast experiments and all of the JEG-3 cell experiments, the control medium contained the same volume of 0.01M phosphate buffered saline (PBS) (pH 7.4) as was used to dissolve the test substance in the experimental media. In the time course studies, the medium was removed and replaced with control or experimental medium each 24 hours during 72–96 hour incubation period. In other experiments, the medium in both control and experimental wells were removed at termination of the experiments after 72 hours incubation.

The spent media were centrifuged and the supernatants stored at −20° C. until hormone assay. In each experiment, all treatments were tested in 3–4 wells. Each variable was tested in at least two separate experiments.

3. Preparation of Decidual Conditioned Medium (DCM)

Decidual conditioned medium (DCM) was prepared by incubating decidual cells ($5-7.5 \times 10^6$/10ml/flask) in 75cm$^2$ cell culture flasks (Costar, Cambridge, Mass.) containing CMRL-1066 medium for 24–72 hours. In the time course experiments, DCM was removed each 24 hours and used for the next 24-hour treatment of trophoblast cells derived from the same placenta as were the decidual cells. In other studies, DCM was removed during the first 36–48 hours of incubation.

After the medium was decanted from decidual cells and centrifuged, the supernatant was collected for use. In dose-response experiments, the different doses of DCM were prepared by dilution with 0.01M PBS buffer.

4. Evaluation of the Active Fraction of DCM

The effect of proteolytic enzyme treatment on DCM was evaluated by incubating DCM for 16 hours at 37° C. with trypsin or chymotrypsinogen-A (Sigma, 40 ug enzyme/mg DCM protein), followed by the addition of 5 ug α-1-antitrypsin(Sigma)/ug trypsin to the treated DCM with incubation at 37° C. for an additional 4 hours. The same weight of bovine serum albumin (BSA, Sigma) as DCM was added to CMRL-1066 medium, which served as a control, and the medium was treated as described above (60 ug enzyme/mg BSA). DCM was also tested after heating to 100° C. for 30 minutes in a water bath.

The approximate molecular size of the active fraction of DCM was evaluated through ultrafiltration and gel chromatography. DCM was ultrafiltered through an Amicon Diaflo Apparatus (Amicon Corp., Lexington, Mass.) with a YM-10 membrane which has a molecular exclusion limit of 10,000. The greater than 10,000 and the less than 10,000 Dalton fractions were tested. In some experiments, 20ml DCM was concentrated by ultrafiltration using an Amicon YM-2 membrane with a cut off 1,000 Daltons, followed by lyophilization of the concentrated DCM. The lyophilized DCM was resuspended in 0.5 ml 0.01 M PBS buffer, pH 7.4 and applied to a 1×25 cm Sephadex G-25 or G-50 column and eluted with the same buffer. Column characteristics were: $V_o$1=10.5 ml, $V_t$=45 ml and 35 ml for G-25 and G-50, respectively. Twenty five drops per fraction were collected. Several contiguous fractions were pooled and tested at a concentration of 25% of the pool for ability to inhibit hCG in the JEG cells.

5. Negative Controls

CMRL-1066 media collected following 36–48 hours of incubation with AV-3 cells ($5 \times 10^6$ cells/10ml/flask), or RPMI-1788 cells ($5 \times 10^6$ cells/10ml/flask), purchased from American Type Tissue Collection (Rockville, Md.), were used as negative controls. For positive control purposes, 0.5mM 8-bromo-cAMP (Sigma) was used to stimulate the JEG or trophoblast cells. Another positive control for the system was composed of incubation of decidual cells for 96 hours in medium derived from trophoblast culture, with measurement of prolactin (PRL) and placental protein 12 (PP12; insulin-like growth factor-I-binding protein) as indices of decidual protein production.

6. Measurements of Hormones and Proteins hCG, human placental lactogen (hPL), PRL, and PP12 in the media were measured by homologous radioimmunoassay methods as previously described by G. D. Braunstein et al., *Am. J. Obstet. Gynecol.* 131:25–32 (1978)); G. D. Braunstein et al., *AM. J. Obstet. Gynecol.* 138:1205–1213 (1980); P. R. P. Salacinski et al., *Anal. Biochem.* 117:136–146 (1981) and E-M. Rutanen, H. Bohn, and M. Seppala, Am. J. *Obstet. Gynecol.* 144:460–463 (1982). Sensitivity of the assays were 1 ng/ml for hCG and hPL, 1.7 ng/ml for PRL,and 7.8 ng/ml for PP12. The protein content of the cells and media were measured by the method of M. M. Bradford in *Anal. Biochem.* 72:248–254 (1976), using bovine serum albumin as a standard and Bio-Rad protein reagents (Bio-Rad Laboratories, Richmond, Calif.). Concentrations of the hormones in the media were expressed as ng/mg protein or ng/well.

7. Statistical Analysis

All results were presented as the mean±SEM. Student's t-test with the Bonferroni correction was used for determining the statistical significance of the difference between control and experimental groups. A $p<0.05$ was considered to be significant.

8. Amino Acid Analysis

Seven separate decidual samples were grown in culture and the media combined. The decidual choriogonadotropin inhibitory protein was purified by ultrafiltration, Sephadex G50 column chromatography, dialysis of the fractions containing the inhibitory protein, followed by concentration by lyophilization, and application onto a low molecular weight SDS polyacrylamide gel. The 8,000–10,000 Dalton band was electrically transblotted to a PVDF membrane (Trans-Blot Transfer Medium; BioRad Labs, Richmond, Calif. 94804) and subjected to amino acid analysis by Pico Tag chemistry using pre-column reaction with PITC (Phenyl isothiocyanate) using the method of Matsudaira (Matsudaira, PT: A Practical Guide to Protein and Peptide Purification for Microsequencing. *Academic Press*, 1989: pp. 5–7). This method does not measure free asparagine, glutamine, cysteine, tryptophan, and may under represent tyrosine. (The amino acid analysis was run on a fee-for-service basis by Dr. Audree Fowler, at UCLA School of Medicine, Department of Biological Chemistry, Los Angeles, Calif. 90024–9842; 213–825–9842).

B. Results

1. Co-Culture of Trophoblast and Decidual Cells

Figure 1:
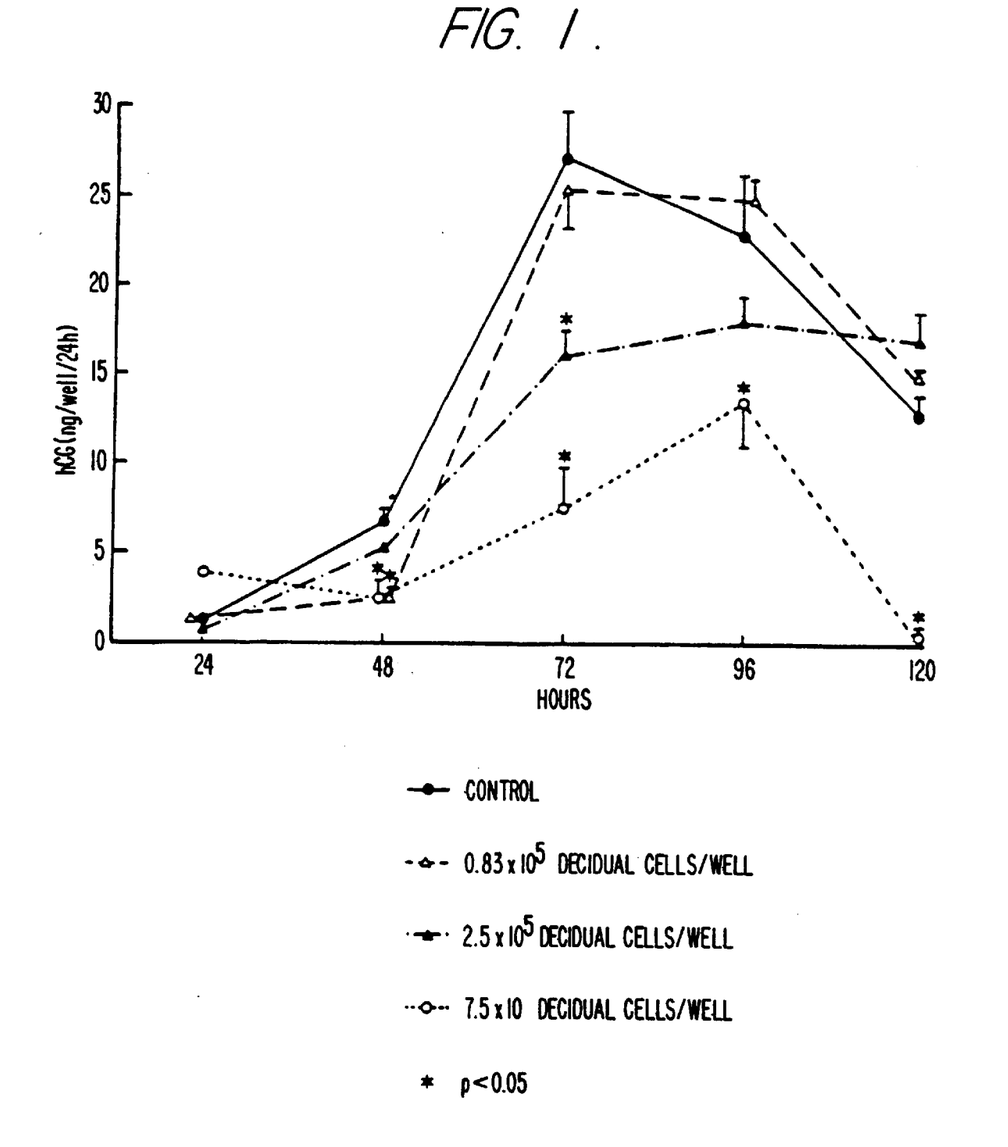
FIG. 1 is a graph showing the relationship between hCG release by trophoblast cells and initial decidual cell concentration in conculture of trophoblast cells ($1 \times 10^6$/well) and decidual cells during 120 hours of incubation.

In the co-culture of trophoblast and decidual cells over 120 hour incubation, $1\times10^6$ trophoblast cells released 112.1±20.2 ng hCG/well/120 hours, while trophoblast plus an average (from 3 experiments) of $5.75\times10^5$ decidual cells released 28.2±4.1 ng hCG/well/120 hour. Thus, the trophoblast cells co-cultured with decidual cells released 75% ($p<0.001$) less hCG than did trophoblast cultured alone. The degree of inhibition of trophoblast hCG secretion by decidual cells was dependent upon the number of decidual cells, with a progressively greater inhibition as the number of decidual cells seeded was increased (FIG. 1).

2. Trophoblast Cells Cultured in DCM-Containing Medium

Figure 2:
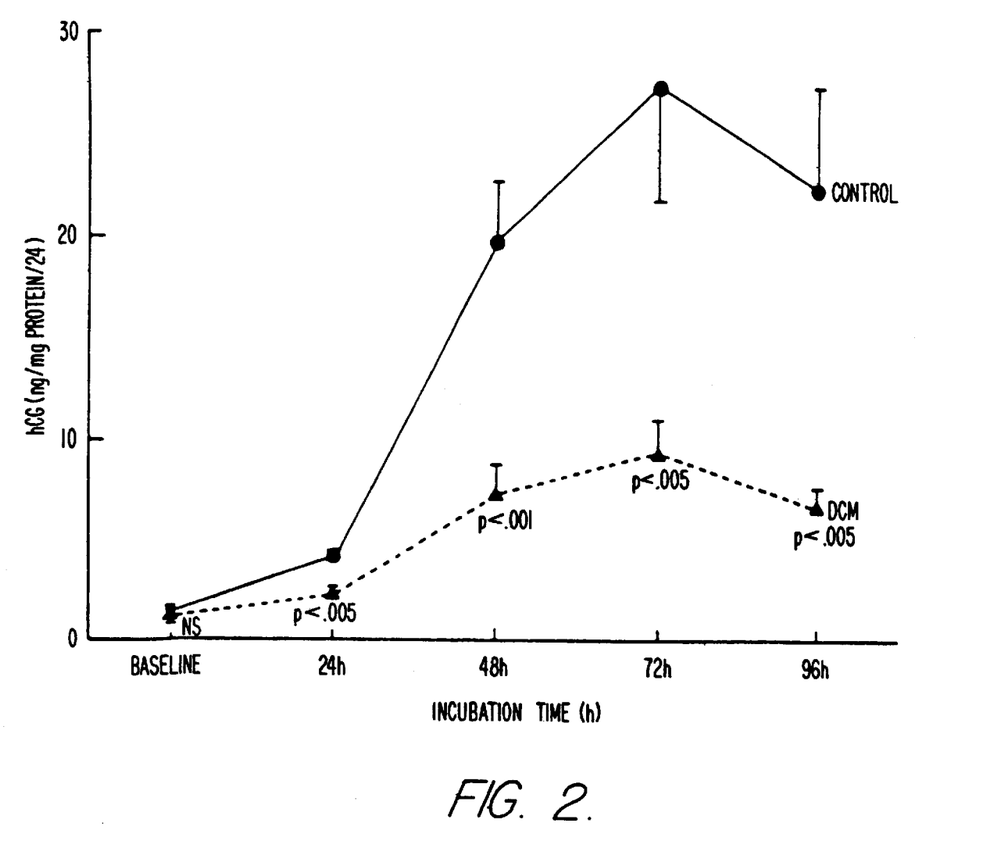
FIG. 2 is a graph showing the time course of inhibition of hCG release from primary trophoblast cell cultures by DCM. Trophoblast cells were exposed to control medium or 50% DCM. The medium was removed and replaced with control medium or DCM each 24 hours during the 96 hour incubation period. Each point presents the mean of 20 wells in three different placental experiments. DCM=Decidual conditioned medium.

Primary trophoblast cells cultured in CRML-1066 medium containing 50% DCM released 45% ($p<0.005$), 64% ($p<0.001$), 66% ($p<0.005$), and 70% ($p<0.005$) less hCG than did control cultures at 24, 48, 72 and 96 hours, respectively (FIG. 2). hPL release from primary trophoblast cultures exposed for 96 hours to 50% DCM was significantly increased (Table I). Decidual cells exposed for 96 hours to 50% trophoblast cell culture medium showed significant stimulation of PRL secretion in the medium compared to control decidual cultures, but PP12 release remained unchanged (Table I).

TABLE I

THE INTERACTION OF TROPHOBLAST AND DECIDUAL CELL ON HORMONES AND PROTEIN RELEASE

| Hormone or Protein (ng/mg protein) | Trophoblast Cell Culture | | Decidual Cell Culture | |
|---|---|---|---|---|
| | Control | Treated with DCM | Control | Treated with Trophoblast Media |
| hCG | 75 ± 14 | 26 ± 4* | – | – |
| hPL | 281 ± 59 | 724 ± 61** | – | – |
| PRL | – | – | 690 ± 81 | 1039 ± 42** |
| PP12 | – | – | 545 ± 22 | 587 ± 47 |

Trophoblast cell (or decidual cell) exposed for 96 hours to 50% DCM (or trophoblast culture medium). Each hormone level in the medium is mean ± SEM of 20 wells from three different placental experiments.
*p < 0.005, **p < 0.001 compared to control.
DCM = Decidual conditioned medium.

Figure 3:
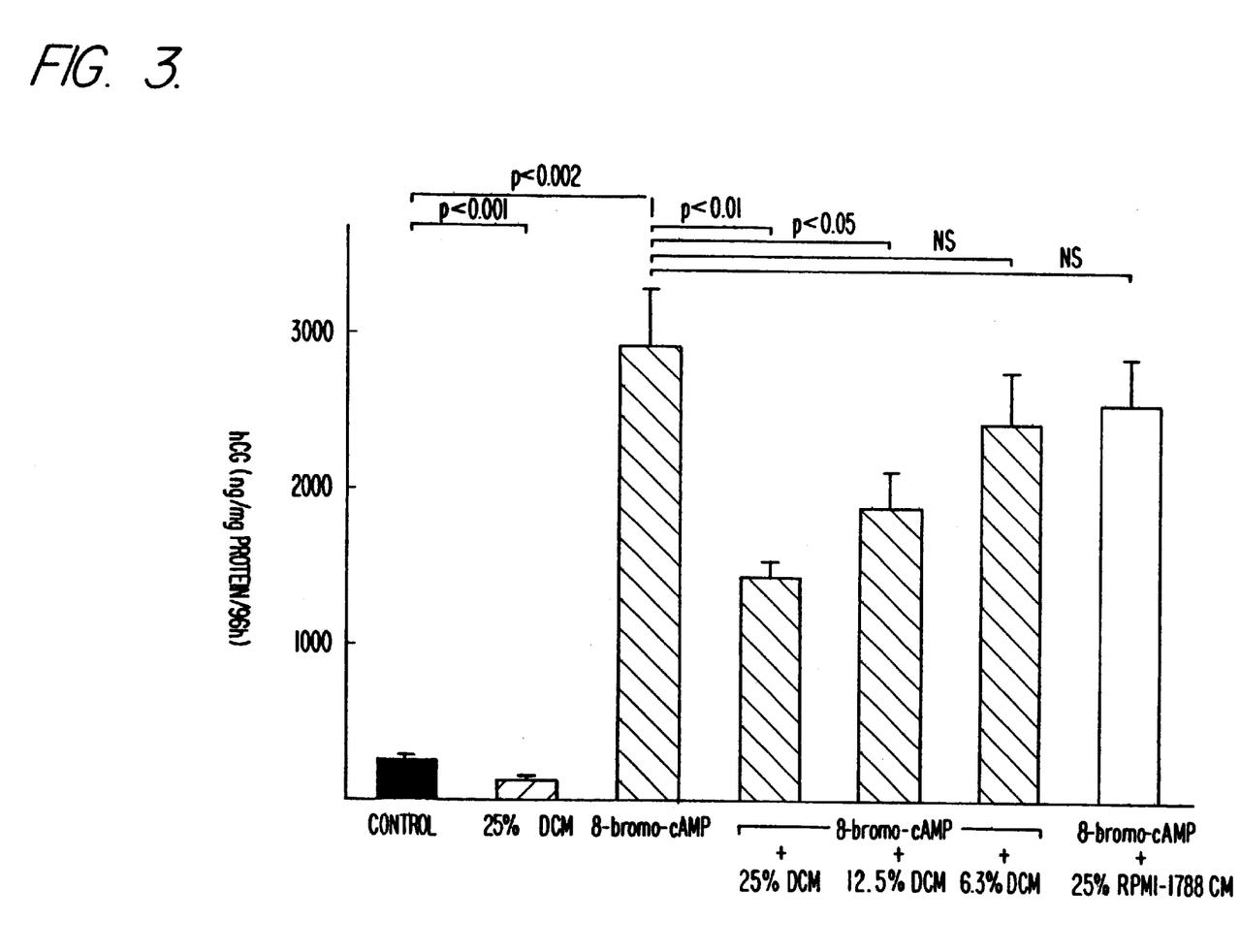
FIG. 3 is a graph showing DCM inhibition of the stimulatory effect of cAMP on hCG secretion by JEG-3 cells. JEG-3 cells were exposed to control media, 25% DCM, 0.5 mM 8-bromo-cAMP plus different doses of DCM, or 0.5 mM 8-bromo-cAMP plus 25% RPMI-1788 cell conditioned media for 72 hours. DCM=Decidual conditioned medium.

3. JEG-Cells Cultured in DCM-Containing Medium JEG-3 cells exposed for 72 hours to 25% DCM also had a significant reduction in hCG secretion into the medium compared to control cultures, but there was neither stimulation nor inhibition of hPL release. Control media obtained from incubation with AV-3 cells or RPMI-1788 cells incubated under the same conditions as the decidual cells for 36–48 hours had no inhibitory effects on hCG release from the JEG-3 cells (Table II). 0.5 mM 8-Bromo-cAMP markedly stimulated hCG secretion; however, DCM, but not conditioned medium from RPMI-1788 cells, significantly reduced the stimulant effect of 8-bromo-cAMP on hCG secretion in a dose-dependent manner (FIG. 3).

TABLE II

THE EFFECTS OF DCM OR CONTROL MEDIA ON hCG RELEASE BY JEG-3 CELLS

| Treatment | hCG (ng/mg protein) |
|---|---|
| Control | 103 ± 6 |
| 25% DCM | 66 ± 12* |
| 25% Boiled DCM | 90 ± 12 |
| Control | 162 ± 34 |
| 25% DCM | 92 ± 10* |
| Medium treated by trypsin | 150 ± 41 |
| 25% DCM treated by trypsin | 134 ± 24 |
| Medium treated by chymotrypsin | 139 ± 18 |
| 25% DCM treated by chymotrypsin | 156 ± 27 |
| Control | 76 ± 6 |
| 25% AV-3 cell medium | 64 ± 7 |
| 25% RPMI cell medium | 73 ± 6 |

JEG-3 cell exposed for 72 hours to DCM with different treatments, or 0.5 mM cAMP or control cell media. The hCG value in media is mean ± SEM of six wells from at least two experiments.

TABLE II-continued

THE EFFECTS OF DCM OR CONTROL MEDIA ON hCG RELEASE BY JEG-3 CELLS

| Treatment | hCG (ng/mg protein) |
|---|---|

DCM = Decidual conditioned medium.
*p < 0.05 compared to control.

4. Dose-Dependent Inhibition of hCG Release

Figure 4:
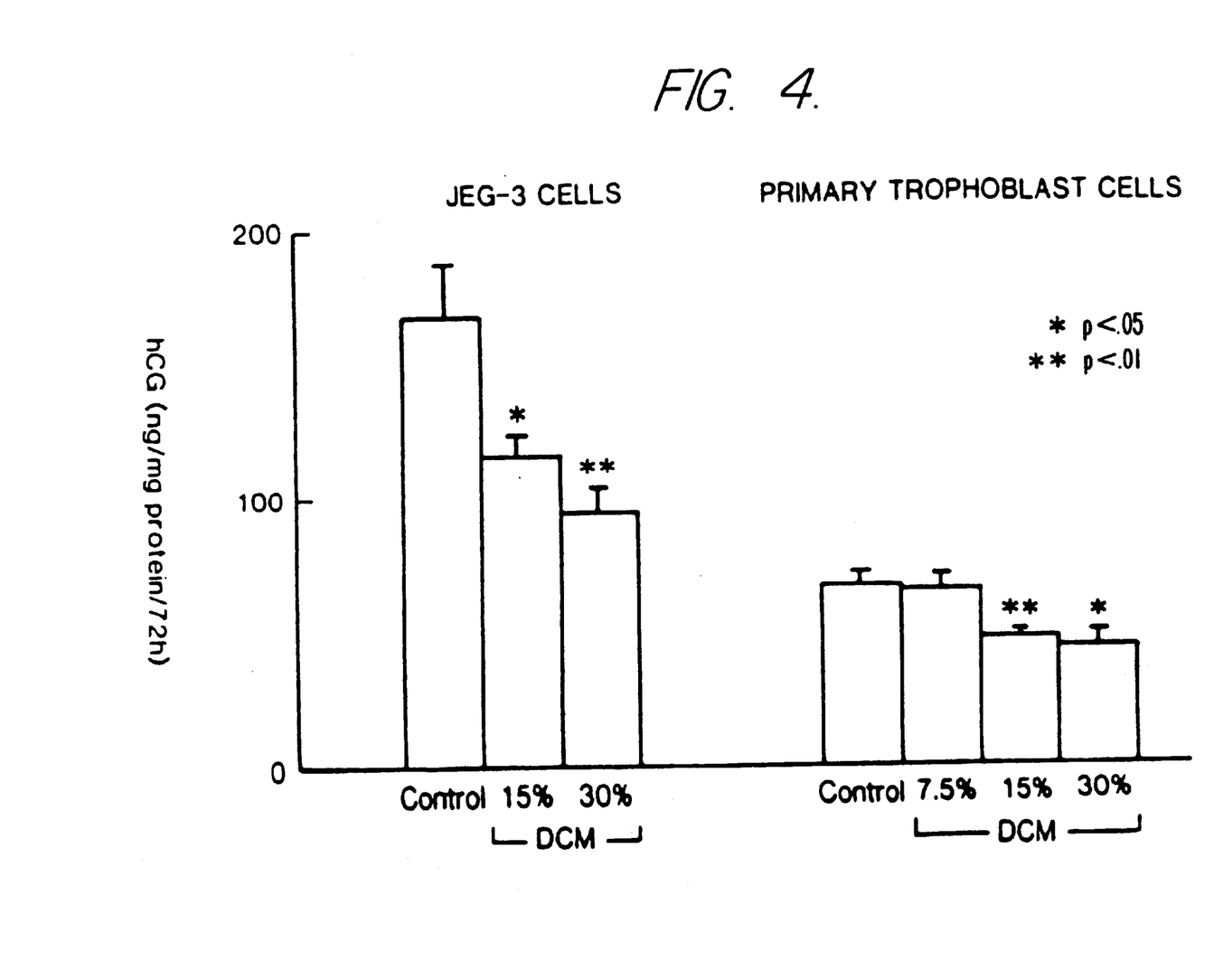
FIG. 4 is a graph showing the dose-response relationship between DCM and hCG release. JEG-3 cells and trophoblast cells were exposed to different concentrations of DCM for 72 hours. Each bar represents mean±SEM of hCG in six wells. DCM=Decidual conditioned medium.
Figure 5:
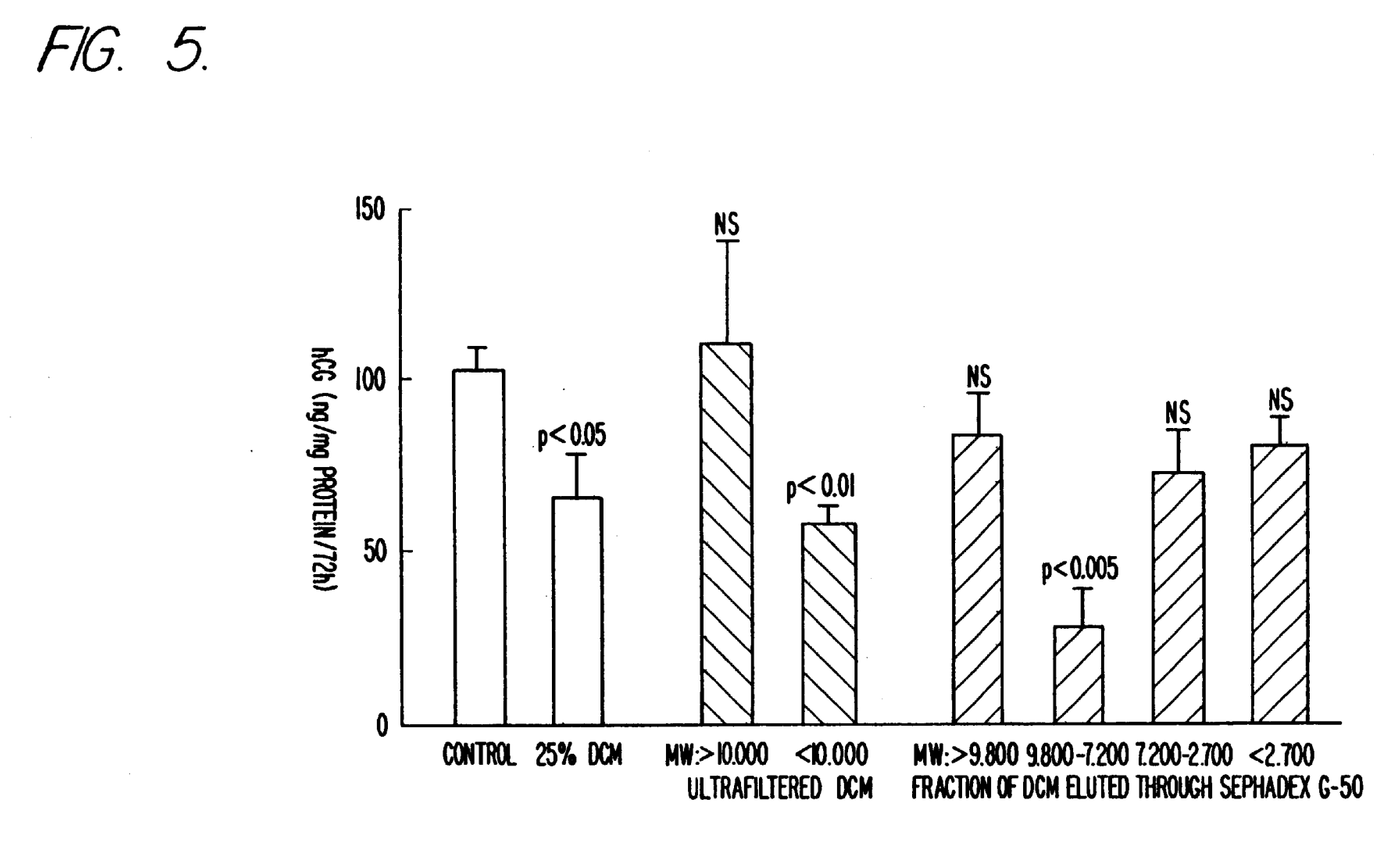
FIG. 5 is a graph showing the inhibitory activity of different fractions of DCM fractionated by ultrafiltration and chromatography. JEG-3 cells were exposed for 72 hours to control medium, 25% DCM, ultrafiltrated (through YM-10) or chromatographed (through Sephadex G-50) fractions of DCM. Each bar represents the mean+SEM of hCG in six wells from at least two experiments. DCM=Decidual conditioned medium.

The inhibitory effect of DCM on hCG release by primary trophoblast cells and JEG-3 cells was dose-dependent as depicted in FIG. 4. The inhibitory activity of DCM was lost following heating at 100° C. for 30 minutes or treatment with trypsin or chymotrypsin (Table II). Following ultrafiltration, the hCG inhibitory activity was found in the less than 10,000 Dalton fraction, and eluted in the 7,200–9,800 Dalton fractions following Sephadex G-50 or G-25 chromatography of the DCM (FIG. 5). This fraction contained 18.6% of the protein eluted from the column.

5. Amino Acid Analysis

The preliminary amino acid composition from 3 separate bands in the 8,000–10,000 Dalton molecular weight range obtained and analyzed as described above are as follows:

TABLE III

| AMINO ACID | # RESIDUES |
|---|---|
| CYSTINE | 0 |
| ASPARTIC ACID | 10–13 |
| GLUTAMIC ACID | 13–17 |
| SERINE | 4–6 |
| GLYCINE | 0 |
| HISTIDINE | 0–1 |
| ARGININE | 2–4 |
| THREONINE | 2–5 |
| ALANINE | 8–10 |
| PROLINE | 4–5 |
| TYROSINE | 0 |
| VALINE | 4 |
| METHIONINE | 1–3 |
| ISOLECINE | 3 |
| LEUCINE | 7 |
| PHENYLALANINE | 2 |
| LYSINE | 0–1 |

The results of our study indicate that the human decidual cell secretes a factor that inhibits hCG release by placental trophoblasts and JEG-3 cells. The inhibition was DCM dose-dependent. The inhibition was also specific for hCG, as DCM (1) did not inhibit total protein synthesis by JEG-3 cells or placental trophoblasts, and (2) stimulated hPL release from primary trophoblast cultures and did not alter hPL secretion by JEG-3 cells (failure of DCM to stimulate hPL release from JEG-3 cells may be due to the paucity of hPL production by these cells). The specificity of this effect is supported further by the absence of hCG inhibition in JEG-3 cells incubated with negative control media.

The similar qualitative hCG secretory pattern of trophoblast cells incubated with DCM and trophoblast cells incubated with control media (FIG. 2) also indicates that the effect is not due to non-specific inhibition, since the peak of hCG release occurred at 72 hours of incubation with or without DCM exposure. We and others have previously demonstrated a similar time course of hCG secretion in primary trophoblast cultures. Y. Kato and G. D. Braunstein, *J. Clin. Endocrinol. Metab.* 68:814–819 (1989) and J. O. Lobo and F. L. Bellino, *J. Clin. Endocrinol. Metab.* 69:868–874 (1989).

Our preliminary characterization of the inhibitory factor indicates that it is a protein with a preliminary amino acid analysis and a molecular weight between about 7,000 and about 10,000 Daltons determined by ultrafiltration and gel chromatography. (A molecular weight up to about 15,000 daltons was measured by SDS polyacrylamide gel electrophoresis. Garfin, D.E. "1-*Dimensional* Gel Electro." MT-Deutch. ed., *Guide to Protein Purification*, Acad. Press 1989 p. 425–441). Yuen and associates have previously suggested that PRL inhibits hCG production in vitro and in vivo. While the decidual cell is a primary source of PRL during pregnancy, it is unlikely that PRL or a fraction of PRL accounted for our results. PRL has a molecular weight of 22,500 Daltons whereas our inhibitory factor has a molecular weight of less than about 10,000 Daltons (or 15,000 Daltons determined as described above). Additionally, the average concentration of immunoreactive PRL in our DCM was approximately 200 ng/ml, which did not inhibit hCG release from trophoblast cells in our studies (Ren and Braunstein, unpublished observations).

Progesterone has also been found by some investigators to inhibit hCG production by placental tissue in vitro. (T. Maruo et al., *Endocrinology* 119:855–864 (1986); E. A. Wilson, M. J. Jawad, and L. R. Dickson, Am. *J. Obstet. Gynecol.* 138:708–713 (1980) and E. R. Barnea and M. Kaplan, *J. Clin. Endocrinol. Metab.* 69:215–217 (1989)). However, progesterone is synthesized by the trophoblast rather than the decidual cells. Since the active hCG inhibitory factor in DCM is destroyed by heat and proteolytic enzymes it is unlikely that progesterone (a steroid hormone) is responsible for the hCG inhibition.

Our data indicate that direct decidual-trophoblast cell contact is not required for regulation of hCG production, although the exact mechanisms by which the decidual cell factor inhibits hCG production is unclear. Since DCM inhibited the stimulant effect of exogenous cAMP on hCG secretion by trophoblasts in our study, DCM may interfere with activation of the cAMP-dependent protein kinases of the placenta, or with transcription of genes encoding the α- and β-subunits of hCG regulated by cAMP.

Trophoblast hPL secretion was stimulated by DCM, a finding that is consistent with those of T. Fay et al., 11th Rochester Trophoblast Conference with the European Placenta Group. Abst. #108 (1988). The different secretory behavior of hCG and hPL in trophoblast cell cultures exposed to the same DCM supports previous observations that the physiological regulation of secretion of different placental protein hormones may differ. It is unknown whether the different action of DCM on hPL and hCG release resides in the same substance or in different substances.

Our results also confirm prior findings by S. Handwerger et al. that placental tissue stimulates PRL production by decidual cells. (S. Handwerger et al., *Endocrinology* 112:1370–1374 (1983) and S. Handwerger et al., *Biochem. Biophys. Res. Commun.* 147:452–459 (1987)). Trophoblast cell culture medium did not, however, change PP12 release from decidual cells indicating that decidual PRL and PP12 regulation are under different control.

In summary, production of hCG by trophoblast and JEG-3 cells is inhibited in a dose-dependent fashion by a protein of about 7,000 to about 10,000 daltons produced by decidual cells. This protein will be useful for investigating abnormalities of human pregnancy, and may provide the basis for diagnostic agents to detect such abnormalities, and for therapeutic agents to induce abortion by decreasing hCG production.

Other and further embodiments of the invention are readily apparent from the above description of the invention, and these embodiments are believed to be within the scope of the invention.

What is claimed is:

1. A method for evaluating inhibition of human chorionic gonadotropin (hCG) production of a subject's trophoblast cells comprising the steps of isolating a regulatory polypeptide
   a) which inhibits, in a dose dependent manner, the production of hCG by human trophoblasts in vitro;
   b) which substantially inhibits the stimulation of hCG secretion by human trophoblasts caused by exogenous cyclic AMP in vitro;
   c) which does not substantially inhibit the production of human placental lactogen (hPL) by human trophoblasts in vitro; and
   d) which exhibits a molecular weight of about 7,000 to about 10,000 daltons, as determined by ultrafiltration and gel exclusion chromatography;
      from human decidual cells of said subject; and quantifying the amount of the regulatory polypeptide produced in vitro by said subject's human decidual cells.

2. The method for evaluating inhibition of hCG production of a subject's trophoblast cells claimed in claim 1 wherein said step of quantifying the amount of regulatory polypeptide includes measuring the inhibition of stimulation of hCG secretion by human trophoblasts caused by exogenous cyclic AMP in vitro by said regulatory polypeptide.

3. The method for evaluating inhibition of hCG production of a subject's trophoblast cells claimed in claim 1 wherein said step of quantifying the amount of regulatory polypeptide includes measuring the promotion of the production of human placental lactogen (hPL) by human trophoblasts in vitro by said regulatory polypeptide.

4. A method for evaluating inhibition of chorionic gonadotropin (hCG) production of a subject's trophoblast cells comprising the steps of isolating a regulatory polypeptide
   a) which inhibits, in a dose dependent matter, the production of hCG by human trophoblasts in vitro;
   b) which substantially inhibits the stimulation of hCG secretion by human trophoblasts caused by exogenous cyclic AMP in vitro;
   c) which does not substantially inhibit the production of human placental lactogen (hPL) by human trophoblasts in vitro; and
   d) which exhibits a molecular weight of about 7,000 to about 10,000 Daltons, as determined by ultrafiltration and gel exclusion chromatography;
      from human decidual cells of said subject; and quantifying the amount of the regulatory polypeptide produced in vivo by said subject's human decidual cells.

5. The method for evaluating inhibition of hCG production of a subject's trophoblast cells claimed in claim 4 wherein said step of quantifying the amount of regulatory polypeptide includes measuring the inhibition of stimulation of hCG secretion by human trophoblasts caused by exogenous cyclic AMP in vivo by said regulatory polypeptide.

6. The method for evaluating inhibition of hCG production of a subject's trophoblast cells claimed in claim 5 wherein said step of quantifying the amount of regulatory polypeptide includes measuring the promotion of the production of human placental lactogen (hPL) by human trophoblasts in vivo by said regulatory polypeptide.

7. The method for evaluating inhibition of hCG production of a subject's trophoblast cells claimed in claim 1 further comprising the step of comparing said quantified polypeptide relative to a reference value.

8. The method for evaluating inhibition of hCG production of a subject's trophoblast cells claimed in claim 4 further comprising the step of comparing said quantified polypeptide relative to a reference value.

* * * * *